(12) United States Patent
Hare et al.

(10) Patent No.: US 7,592,138 B2
(45) Date of Patent: Sep. 22, 2009

(54) IDENTIFICATION OF A GENE EXPRESSION PROFILE THAT DIFFERENTIATES ISCHEMIC AND NONISCHEMIC CARDIOMYOPATHY

(75) Inventors: Joshua M. Hare, 928 ½ Fell St., Baltimore, MD (US) 21231; Michelle M. Kittleson, Stevenson, MD (US)

(73) Assignee: Joshua M. Hare, Miami, FL (US)

( * ) Notice: Subject to any disclaimer, the term of this patent is extended or adjusted under 35 U.S.C. 154(b) by 305 days.

(21) Appl. No.: 11/012,778

(22) Filed: Dec. 15, 2004

(65) Prior Publication Data

US 2005/0158756 A1 Jul. 21, 2005

Related U.S. Application Data

(60) Provisional application No. 60/529,834, filed on Dec. 16, 2003.

(51) Int. Cl.
C12Q 1/68 (2006.01)
(52) U.S. Cl. .......................................................... 435/6
(58) Field of Classification Search ....................... None
See application file for complete search history.

(56) References Cited

U.S. PATENT DOCUMENTS

| | | |
|---|---|---|
| 2003/0036070 A1 | 2/2003 | Chakravarti |
| 2003/0219760 A1 | 11/2003 | Gordon et al. |
| 2004/0115671 A1 | 6/2004 | Zlokovic et al. |

OTHER PUBLICATIONS

Tusher et al. (2001) vol. 98; pp. 5116-5121).*
Towbin et al., Molecular genetics of left ventricular dysfunction, *Curr Mol. Med.* Mar. 2001;1(1):81-90.
Kittleson et al., Identification of a gene expression profile that differentiates between ischemic and nonischemic cardiomyopathy, *Circulation* (2004) 110:3444-3451.
Alizadeh et al., Distinct types of diffuse large B-cell lymphoma identified by gene expression profiling, *Nature* vol. 403 Feb. 3, 2000, p. 503-511.
Yung et al., Gene expression profiles in end-stage human idiopathic dilated cardiomyopathy: altered expression of apoptotic and cytoskeletal genes, *Genomics* 83 (2004) p. 281-297.
Steenman et al., Transcriptomal analysis of failing and nonfailing human hearts, *Physiol. Genomics* 12: 97-112 (2003).
Kääb et al., Global gene expression in human myocardium-oligonucleotide microarray analysis of regional diversity and transcriptional regulation in heart failure, *J. Mol. Med.* 82:308-316 (2004).
Boheler et al., Sex-and age-dependent human transcriptome variability: Implications for chronic heart failure, *PNAS* Vo. 100, p. 2754-2759 (2003).
Hwang et al., Microarray gene expression profiles in dilated and hypertrophic cardiomyopathic end-stage heart failure, *Physiol Genomics* 10:31-44 (2002).

Chen et al., Alterations of gene expression in failing myocardium following left ventricular assist device support, *Physiol Genomics* 14: 251-260 (2003).
Hall et al., Genomic profiling of the human heart before and after mechanical support with a ventricular assist device reveals alterations in vascular signaling networks, *Physiol Genomics* 17: 283-291 (2004).
Chen et al., Novel Role for the Potent Endogenous Inotrope apelin in Human Cardiac Dysfunction, *Circulation*; 108:1432-1439 (2003).
Blaxall et al., Differential Gene Expression and Genomic Patient Stratification Following Left Ventricular Assist Device Support, *Journal of the American College of Cardiology*, vol. 41, No. 7 (2003).
Golub et al., Molecular Classification of Cancer: Class Discovery and Class Prediction by Gene Expression Monitoring, *Science* vol. 286 Oct. 15, 1999, p. 531-537.
Felker et al., *Underlying causes and long-term survival in patients with initially unexplained cardiomyopathy*, vol. 342 No. 15 (2002) p. 1077-1084.
Dries et al., Prognostic impact of diabetes mellitus in patients with heart failure according to the etiology of left ventricular systolic dysfunction, *Journal of the American College of Cardiology*, vol. 38, No. 2 (2001).
Felkder et al., Heart Failure Etiology and Response to Milrinone in Decompensated Heart Failure, *Journal of the American College of Cardiology*, vol. 41, No. 6 (2003).
Kittleson et al., Development of Circulatory-renal Limitations to Angiotensin-Converting Enzyme Inhibitors Identifies Patients with Severe Heart Failure and Early Mortality, *Journal of the American College of Cardiology*, vol. 41, No. 11 (2003).
Follath et al., Etiology and response to drug treatment in heart failure, *JACC* vol. 32, No. 5, Nov. 1, 1998:1167-72.
Reynolds et al., MADIT II (Second Multicenter Automated Defibrillator Implantation Trial) Debate Risk Stratification, Costs, and Public Policy, *Circulation*, 108:1779-1783 (2003).
Felker et al., A standardized definition of ischemic cardiomyopathy for use in clinical research, *Journal of the American College of Cardiology*, vol. 39, No. 2 (2002).
Eisen et al., Cluster analysis and display of genome-wide expression patterns, *Proc. Natl. Acad. Sci.*, vol. 95, pp. 14863-14868 (1998).

(Continued)

*Primary Examiner*—Kenneth R. Horlick
*Assistant Examiner*—David C Thomas
(74) *Attorney, Agent, or Firm*—Arnold & Porter LLP

(57) ABSTRACT

A method of preparing a gene expression prediction profile for distinguishing ischemic and nonischemic cardiomyopathy comprises the steps of obtaining clinical specimens from patients suffering from ischemic or nonischemic cardiomyopathy, isolating nucleic acid sequences from at least a plurality of said specimens, obtaining a gene expression level corresponding to each individual of said nucleic acid sequence by a gene expression profiling method, identifying genes having differences in gene expression by comparing the gene expression level of an ischemic specimen with the gene expression level of a nonischemic specimen, and identifying a gene expression prediction profile comprises genes identified as having differences in gene expression so that said prediction profile distinguishes ischemic and nonischemic cardiomyopathy.

12 Claims, 3 Drawing Sheets

OTHER PUBLICATIONS

Mukherjee et al., Estimating dataset size requirements for classifying DNA microarray data, *Journal of Computational Biology*, vol. 10, No. 2, p. 119-142 (2003).

Tibshirani et al., diagnosis of multiple cancer types by shrunken centroids of gene expression, PNAS vol. 99, No. 10, p. 6567-6572 (2002).

Liu et al., Microarrays and ClinicalInvestigations, N. Engl. J. Med. 350; 16 (2004).

Cook et al., DNA Microarrays Implications for Cardiovascular Medicine, *Circulation Research*, p. 559-564 (2002).

Ladilov et al., Role of protein phosphatases in hypoxic preconditioning, *Am J. Physiol Heart Circ Physiol*. 283:H1092-H1098 (2002).

Ng et al., Activation of signal transducer and activator of transcription (STAT) pathways in failing human hearts, *Cardiovascular Research* 57 p. 333-346 (2003).

Shulman et al., Urocortin protects the heart from reperfusion injury via upregulation of p42/p44 MAPK signaling pathway, *Am J. Physiol Heart Circ. Physiol* 283:H1481-H1488 (2002).

Serneri et al., Selective upregulation of cardiac endothelin system in patients with ischemic but not idiopathic dilated cardiomyopathy, *Circulation Research* Mar. 3, 2000.

Kajstura et al., Myocyte proliferation in end-stage cardiac failure in humans, *Proc. Natl. Acad. Sci.* vol. 95, pp. 8801-8805 (1998).

Simon et al., Pitfalls in the use of DNA microarray data for diagnostic an prognostic classification, *Journal of the National Cancer Institute*, vol. 95, No. 1, (2003).

Rosenwald et al., The use of molecular profiling to predict survival after chemotherapy for diffuse large -B-cell lymphoma, *The New Eng. Journ. of Med.*, vol. 346 No. 25 (2002).

Vijver et al., A gene-expression signature as a predictor of survival in breast cancer, *The New England Journal of Medicine*, vol. 347 No. 25 (2002).

Valk et al., Prognostically useful gene-expression profiles in cute myeloid leukemia, *New England Journal of Medicine*, 350;16 (2004).

Bullinger et al., use of gene-expression profiling t identify prognostic subclasses in adult acute myeloid leukemia, *The New England Journal of Medicine*, vol. 350 No. 16 (2004).

Barrans et al., global gene expression profiling of end-stage dilated cardiomyopathy using a human cardiovascular-based cDNA microarray, *American Journal of Pathology* vol. 160, No. 6 (2002).

Tan et al., The gene expression fingerprint of human heart failure, *PNAS*, vol. 99 No. 17 (2002).

Butte, A., "The Use and Analysis of Microarray Data", *Nature Reviews. Drug Discovery*, 1(12):951-960 (2002).

\* cited by examiner

IDENTIFICATION OF A GENE EXPRESSION PROFILE THAT DIFFERENTIATES ISCHEMIC AND NONISCHEMIC CARDIOMYOPATHY

RELATED APPLICATION

This application claims priority of U.S. provisional patent application Ser. No. 60/529,834, filed Dec. 16, 2003, the content of which is hereby incorporated by reference in its entirety.

BACKGROUND OF THE INVENTION

Field of the Invention

This invention relates to cardiomyopathy and especially to diagnosis and prognosis of ischemic and nonischemic cardiomyopathy. Most particularly, this invention relates to a diagnostic method to differentiate ischemic from nonischemic cardiomyopathy based on a gene expression profile of the heart tissue being evaluated. This invention also relates to a method of gene profiling and to a gene expression prediction profile prepared in accordance with said method.

Gene expression profiling holds great promise as a tool to refine diagnostic and prognostic accuracy in a variety of diseases. This technique has enjoyed widespread success in solid and hematologic malignancies and may soon be employed in clinical trials. (Alizadeh A A et al., Nature (2000); Lapointe J., et al., Proc Natl Acad Sci. (2004); Tibshirani R., et al., Proc Natl Acad Sci. (2002); Dhanasekaran S M, et al., Nature (2001); Pomeroy, et al., Nature (2002); Van de Vijver M J, et al., N Engl J. Med. (2002); Golub T R, et al., Science (1999); Rosenwald A., et al., N Engl J. Med. (2002). In contrast, while the ability to refine diagnosis, particularly with regard to ischemic etiology, and predict patient outcome is of tremendous importance in myocardial diseases, the application of gene expression profiling for this purpose is in its earliest stages. To date, small studies have demonstrated that gene expression differs between failing and nonfailing hearts, (Barrans J D., et al., Am J Pathol. (2002); Tan F L., et al., Proc Natl Acad Sci. (2002); Yung C K., et al., Genomics; Steenman M., et al., Physiol Genomics (2004)) dilated and hypertrophic cardiomyopathy, (Hwang J J, Allen P D, Tseng G C et al., Physiol Genomics (2002)) and before and after placement of a ventricular assist device, (Chen Y., et al., Physiol Genomics (2003); Hall J L., et al., Physiol Genomics (2003); Chen M M., et al., Circulation; Blaxal B C, et al., J AM Coll Cardiol (2003)). These studies focused on the identification of novel genetic pathways. The application of gene expression profiling to distinguish clinically relevant cardiomyopathic disease subtypes has not previously been performed and is considered controversial, due to the contention that, unlike tumors, there is a final common pathway independent of etiology for the progression of myocardial disease.

Ischemic cardiomyopathy is defined as evidence of myocardial infarction on histology of the explanted heart. Gene expression profiling would serve as a valuable adjunct to imaging and metabolic tools in the diagnosis of ischemic cardiomyopathy. Despite similar presentations, ischemic and nonischemic cardiomyopathy are distinct diseases. Patients with ischemic cardiomyopathy have decreased survival compared to their nonischemic counterparts (Felker G M, et al., N Engl J Med. (2000); Felker G M, et al., J AM Coll Cardiol. (2003); Dries D L, et al., J Am Coll Cardiol. (2001)) and respond differently to therapies, (Kittleson M, et al., J Am Coll Cardiol. (2003); Doval H C, et al., Lancet (1994); Singh S N, et al., N Engl J Med. (1995); Reynolds M R, et al., Circulation (2003)). An ischemic gene expression profile would offer diagnostic insight, especially in patients with heart failure out of proportion to their coronary artery disease. The proportion of such patients is estimated to be up to 11% in one observational study (Felker G M, et al., J Am Coll Cardiol. (2002)). The ability to tailor treatments to specific patients by identifying those who would most benefit, is of critical importance in heart failure patients. (Reynolds M R, Circulation (2003)).

A prior study noted differences in gene expression in ischemic versus nonischemic cardiomyopathy samples following LVAD (left ventricle assist device) support. However, that study did not create or prospectively validate a prediction rule, (Blaxall B C, et al., J Am Coll Cardiol. (2003)) Another study compared the gene expression profiles of ischemic and nonischemic cardiomyopathy samples and found no differentially expressed genes (Steenman M, et al., Physiol Genomics. (2003)). But that study used pooled samples from only two ischemic and two nonischemic cardiomyopathy patients, and it is likely that this study did not have adequate power to detect changes in gene expression (Mukherjee S, et al., J Comput Biol. (2003)).

Another study shows that the differential gene expression between failing and nonfailing hearts has been attributed to age and gender differences, (Boheler K R, et al., Proc Natl Acad Sci USA. (2003)). However, this analysis has not been extended to ischemic and nonischemic cardiomyopathy. Other studies have also shown that failing hearts exhibit changes in gene expression following LVAD support (left ventricle assist device). (Chen Y., et al., Physiol Genomics (2003); Hall J L., et al., Physiol Genomics (2004); Chen M M., et al., Circulation (2003); Blaxal B C, et al., J AM Coll Cardiol. (2003)). In addition, gene expression analysis was considered hypothesis-generating until validated by another technique. (Cook S A, et al., Circ Res. (2002)).

Our major new finding is that a gene expression-based signature accurately distinguishes between ischemic and nonischemic etiologies of cardiomyopathy. Gene expression profiles have been successfully correlated with etiology or clinical outcome in oncology (Alizadeh M et al., Nature (2000); Lapointe J., et al., Proc Natl Acad. Sci. (2004); Tibshirani R., et al., Proc Natl Acad. Sci. (2002); Dhanasekaran S M, et al., Nature (2001); Pomeroy, et al., Nature (2002); Van de Vijver M J, et al., N Engl J. Med. (2002); Golub T R, et al., Science (1999); Rosenwald A., et al., N Engl J. Med. (2002); Hastie T, et al., Genome Biol. (2000) and renal allograft rejection, (Sarwal M, et al., N Engl J. Med. (2003)). Expression profile-based prognostic tools are in clinical trials in oncology. There is an equal need to refine diagnostic and prognostic techniques in myocardial diseases. Our findings demonstrate that gene expression profiling can accurately identify disease etiology. This has substantial clinical implications and strongly supports ongoing efforts to incorporate expression-profiling based biomarkers in determining prognosis and response to therapy.

SUMMARY OF THE INVENTION

An object of the present invention is to provide a gene expression profile that can discriminate between common causes of heart failure in patients with end-stage cardiomyopathy. We have established that the methodology to achieve this end is highly generalizable to data obtained in different laboratories.

Another object of the present invention is to establish that molecular signatures can be used to refine the diagnostic evaluation and management of heart failure, where treatment and prognosis decisions may vary based on disease etiology (Felker G M, et al., *N Engl J. Med.* (2000); Felker G M, et al., *J Am Coll Cardiol* (2003); Dries D L, et al., *J Am Coll Cardiol.* (2001); Kittleson M, et al., *J Am Coll Cardiol.* (2003); Doval H C, et al., *Lancet* (1994); Singh S N, et al., *N Engl J Med.* (1995); Follath F, et al., *J Am Coll Cardiol.* (1998)).

More specifically, the present invention is directed to a method of preparing a gene expression prediction profile for distinguishing ischemic and nonischemic cardiomyopathy, comprising the steps of:

obtaining clinical specimens from patients suffering from ischemic or nonischemic cardiomyopathy;

isolating nucleic acid sequences from at least a plurality of said patients;

obtaining a gene expression level corresponding to each individual of said nucleic acid sequence by a gene expression profiling method;

identifying genes having statistically significant difference in gene expression by comparing the gene expression level of an ischemic specimen with the gene expression level of a nonischemic specimen, and identifying a gene expression prediction profile that distinguishes ischemic and nonischemic cardiomyopathy.

The present invention is also directed to a method of diagnosis for differentiating ischemic and nonischemic cardiomyopathy, comprising the steps of:

obtaining a clinical specimen from a patient having cardiomyopathy;

isolating nucleic acid sequences from said specimen;

obtaining a gene expression level corresponding to said nucleic acid sequence by a gene expression profiling method;

comparing the gene expression level of said specimen with a gene expression prediction profile prepared in accordance with the method described above to determine ischemic or nonischemic cardiomyopathy by performing a prediction analysis.

The present invention is further directed to a gene expression prediction profile prepared in accordance with a method comprising the steps of:

obtaining clinical specimens from patients suffering from ischemic or nonischemic cardiomyopathy;

isolating nucleic acid sequences from at least a plurality of said patients;

obtaining a gene expression level corresponding to each individual of said nucleic acid sequence by a gene expression profiling method;

identifying genes having differences, preferably statistically significant differences in gene expression by comparing the gene expression level of an ischemic specimen with the gene expression level of a nonischemic specimen, and identifying a gene expression prediction profile comprising genes that distinguishes ischemic and nonischemic cardiomyopathy.

The present invention is further directed to a method of treating ischemic or nonischemic cardiomyopathy, comprising the step of diagnosing for differentiating ischemic and nonischemic cardiomyopathy. The diagnosis comprises the steps of:

obtaining a clinical specimen from a patient having cardiomyopathy;

isolating nucleic acid sequences from said specimen;

obtaining a gene expression level corresponding to said nucleic acid sequence by a gene expression profiling method;

comparing the gene expression level of said specimen with a gene expression prediction profile prepared in accordance with the method of claim 1 to determine ischemic or nonischemic cardiomyopathy by performing a prediction analysis.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
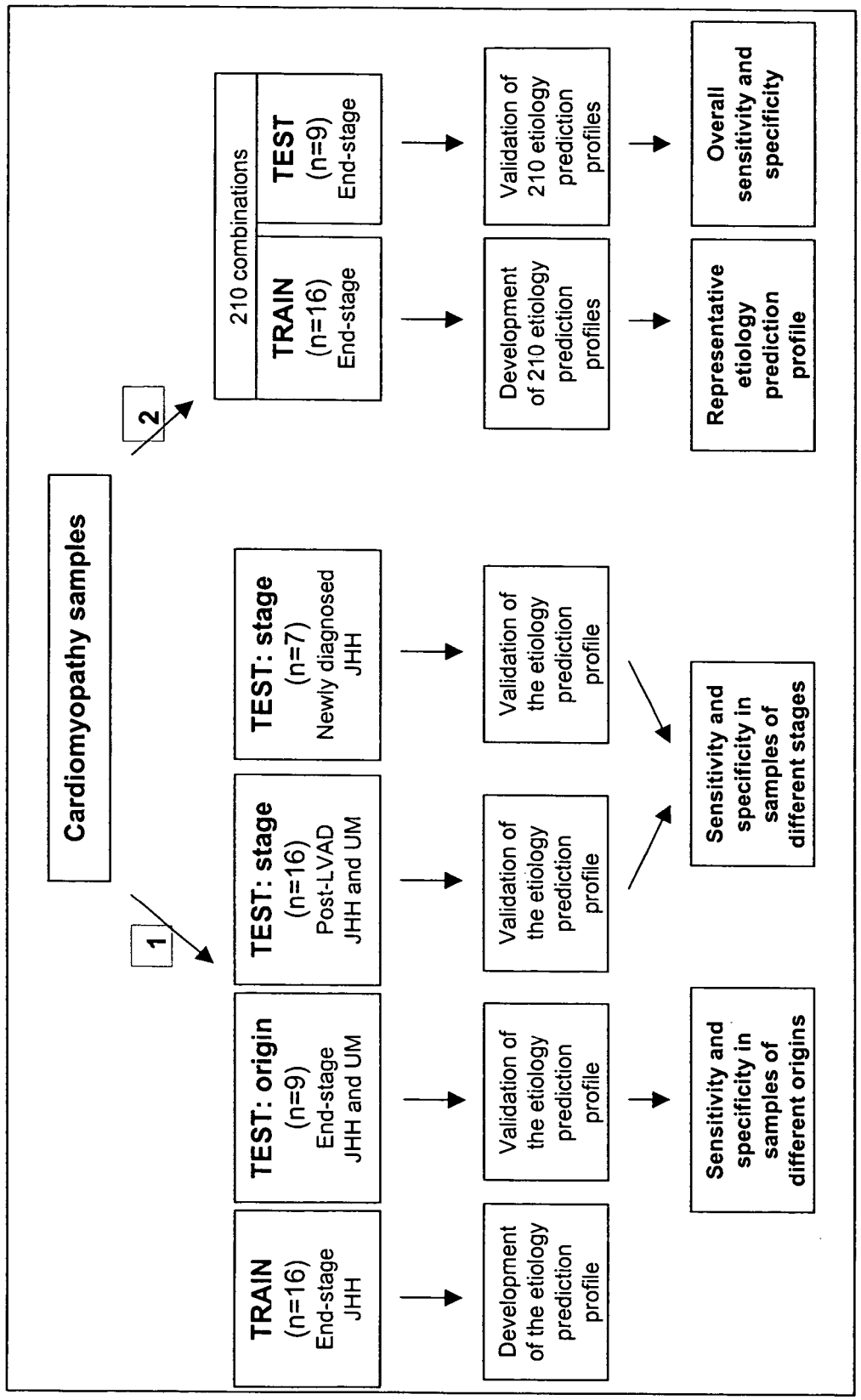
FIG. 1 illustrates the separation of end-stage cardiomyopathy samples into a training set (used to identify the gene expression prediction profile), a test set (used to assess the accuracy of the prediction profile), and post-remodeling samples. The overall predictive accuracy was assessed by examining 210 combinations of training and test set samples.

As used herein, the term gene expression prediction profile or molecular signature or gene expression-based signature means a known expression profile of a set of genes to which an unknown gene expression profile of a new set of genes can be compared or evaluated.

The term clinical specimens mean samples obtained from human heart muscle in various ways.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

As used herein, the term expression profiling method is a method of detecting the level of gene expression based on technologies such as DNA microarray, Spotted array, cDNA array, and reverse transcription polymerase chain reaction (RT-PCR).

As used herein, the term random partitioning of the clinical specimens or samples refers to a method of grouping and matching the samples to obtain all possible outcomes resulting from the grouping and matching.

The term prediction analysis generally refers to an analytical method for identifying a gene expression prediction profile. Specifically, the term refers to obtaining a set of genes (also described as a "molecular signature") from a new and unknown sample, that, by comparing the expression level of the genes in this set in the new sample with the gene expression of a known gene expression prediction profile, allows one to determine the group to which the new and unknown sample belongs. The expression level of the genes in the set are sufficiently and consistently different within the groups so as to allow distinguishing to which group a new sample belongs.

The present invention employs a variety of methodologies in connection with establishment of a gene expression profile. While the methodologies employed in the present invention, such as clinical sample collection, nucleic acid sample preparation, DNA microarray technologies, and statistical analysis associated with gene profile analysis are generally available, diagnosis and treatment of ischemic or nonischemic cardiomyopathy based on gene expression profiling were not considered feasible until a group of genes were isolated and identified to accurately discriminate ischemic from nonischemic heart failure.

The invention generally includes the steps as described herebelow.

Patients and Clinical Specimens

To generate a gene expression prediction profile that can provide general prediction, diagnosis and/or prognosis, and treatment based on such diagnosis, clinical specimens are collected from the myocardial tissues of patients who have experienced ischemic or nonischemic cardiomyopathy.

In a preferred embodiment, all patients from whom the myocardial tissues were obtained that had ischemic cardiomyopathy exhibited severe coronary artery disease (>75% stenosis of the left anterior descending artery and at least one other epicardial coronary artery) and/or a documented history of a myocardial infarction. (Hare J M, et al., *J Am Coll Cardiol.* (1992); Felker G M, et al., *J Am Coll Cardiol.* (2003)) Nonischemic patients had no history of myocardial infarction, revascularization, or coronary artery disease.

Preferably the myocardial tissues from surgery are immediately frozen in liquid nitrogen and stored at −80° C. tissues can also be stored with other methods.

Expression Profiling Method

To establish an expression profile of myocardial genes, a DNA microarray may be used. Myocardial RNA may be isolated from the frozen samples using the Trizol reagent and Qiagen RNeasy columns. Double-stranded cDNA may be synthesized from 5 μg RNA using the SuperScript Choice system (Invitrogen Corp, Carlsbad, Calif.). Each double-stranded cDNA may be subsequently used as a template to make biotin-labeled cRNA. 15 μg of fragmented, biotin-labeled cRNA from each sample was hybridized to an Affymetrix U133A microarray (Affymetrix, Santa Clara, Calif.). Affymetrix chip processing was performed. The U133A microarray allows detection of 21,722 transcripts (15,713 full length, 4,534 non-expressed sequence tags (ESTs) and 1,475 ESTs). The quality of array hybridization may be assessed by the 3' to 5' probe signal ratio of GAPDH and β-actin. A ratio of 1-1.2, indicates an acceptable RNA preparation.

While a DNA microarray for obtaining a gene expression profile is preferred, other expression methods known to a person of ordinary skill in the art, such as Spotted array, cDNA array, and RT-PCR, may also be used to obtain substantially the same results.

Data Normalization

The purpose of data normalization is to convert probe-set data from the microarray hybridization (the raw data obtained from the microarray) to gene expression values. The microarray contains multiple probes for each given transcript, the intensity of hybridization to each of these probes must be combined to create a single quantitative value for the expression of each transcript. In addition, normalization allows for correction for variation within chips and across samples so that data from different chips can be simultaneously analyzed. The robust multi-array analysis (RMA) algorithm, which is described in references (Irizarry R A, et al., *Biostatistics* (2003) and Irizarry R A, et al., *Nucleic Acids Res.* (2003)), may be used to pre-process the Affymetrix probe set data into gene expression levels for all samples. The contents of Irizarry R A, et al., *Biostatistics* (2003); Irizarry R A, et al., *Nucleic Acids Res.* (2003) are incorporated by reference in their entirety. Although other methods may be used to normalize the data, such as using Affymetrix's default preprocessing algorithm (MAS 5.0), RMA is preferred, which results in classifiers with better predictive power. (Irizarry R A, et al., *Nucleic Acids Res.* (2003)).

Filtering

In order to create the gene expression prediction profile using genes that are differentially expressed in ischemic versus nonischemic samples, a statistical analysis for identifying genes that exhibit changes in gene expression, preferably statistically significant changes in gene expression, between ischemic and nonischemic samples was performed. For this purpose, Significance Analysis of Microarrays (SAM) is preferred. Reference (Tusher V G, et al., *Proc Natl Acad Sci USA*. (2001)) provides details of SAM analysis, the content of which is incorporated by reference in its entirety. SAM identifies genes with changes, preferably statistically significant changes in expression by assimilating a set of gene-specific tests (similar to the t-test) which we will refer to as the SAM-statistics. For any given threshold, a resampling procedure is used to estimate false discovery rates (FDR) of lists of genes for which the SAM-statistic is bigger than this threshold. At a FDR of 0.1%, there were 3332 differentially expressed genes between ischemic and nonischemic hearts. These 3332 genes were then subject to further analysis. Other statistical methods known to a person of ordinary skill in the art may also be used to accomplish the same objective.

Prediction Analysis

To test consistency between an expression profile relative to ischemic or nonischemic cardiomyopathy, a classification algorithm based on the methodology used by the Prediction Analysis of Microarrays software PAM (Tibshirani R, et al., *Proc Natl Acad Sci USA*. (2002)) was employed. By doing so, a gene expression profile that distinguishes ischemic from nonischemic cardiomyopathy samples is identified. While other known methods may be used for the same purpose, PAM is preferred. PAM is a supervised classification method that defines a score for each gene, representative of its contribution to predictive power. Given a set of genes, PAM defines a prediction rule based on classification of the training set that is then applied to the test set. Details about PAM are provided in reference Tibshirani R, et al., *Proc Natl Acad Sci USA*. (2002), the content of which is incorporated by reference in its entirety.

Statistical Analysis

To assess if the accuracy of the etiology prediction profile is affected by baseline clinical covariates (including age, gender, systolic function, and medication use) as well as differences in etiology, individuals from which the clinical specimens are obtained were stratified, based on these covariates, and the predictive accuracy was assessed.

Continuous variables may be summarized by the median and quartiles and groups may be compared using the Wilcoxon rank sum test. Categorical variables may be summarized by proportions and compared using Fisher's exact test.

Prediction accuracy is determined based on the sensitivity and specificity of the prediction, where sensitivity is the proportion of ischemic cardiomyopathy samples correctly classified by gene expression profiling, and specificity is the proportion of nonischemic cardiomyopathy samples correctly classified.

The present invention yields a prediction tool that was generalizable to samples from different laboratories, and for ischemic non-ischemic cardiomyopathy, the prediction tool was independent of disease severity.

To determine if the etiology prediction profile was affected by differences in clinical characteristics between ischemic and nonischemic cardiomyopathy patients, we stratified our analysis based on clinical covariates mentioned in Table 1 below and found that the sensitivity and specificity of our analysis was not affected. This supports the idea that the excellent predictive accuracy of our method is not an artifact of differences in baseline characteristics.

We created a gene expression profile in end-stage cardiomyopathy samples and tested the profile in samples of comparable stage. We also tested the profile in post-LVAD samples of nonischemic hearts where the prediction profile performed perfectly in classifying ischemic or nonischemic cardiomyopathy, although only one of three ischemic post-LVAD samples was correctly classified. This suggests that ischemic hearts exhibit more extensive changes in gene expression following LVAD support than nonischemic hearts. While this seems to be in contrast to a recent study which determined that nonischemic cardiomyopathy patients exhibited greater changes in gene expression, (Blaxall B C, et al., *J Am Coll Cardiol*. (2003)), the duration of LVAD support in that study was relatively short (mean (±SD) of 57±15 days), compared with our present study (190±151 days), and this may have affected changes in gene expression.

Unlike the majority of studies in cardiology, where microarray analysis is concentrated on the discovery of novel genetic pathways, our analysis is focused on clinical prediction. Thus, our validation involved application of the identified gene expression prediction profile to classify independent samples. Using this approach, well-validated in the cancer literature, (Tibshirani R, et al., *Proc Natl Acad Sci USA* (2002); Van de Vijver M J, et al., *N Engl J Med*. (2002); Golub T R, et al., *Science*. (1999)) we have determined the etiology of independent samples with excellent accuracy over a wide range of combinations of test set samples.

To the best of the inventor's knowledge this study is the first proof that microarray analysis can contribute substantially to improving clinical diagnosis and optimizing therapy based on gene expression profiling in heart tissues. The present study also forms a basis for future studies using molecular profiling to differentiate heart failure by clinically relevant parameters, including prognosis and response to therapy.

The invention may be further illustrated by the following examples, which are not limitations to the present invention.

Example 1

Patients and Clinical Specimens

The study sample comprised 41 samples from 27 patients with cardiomyopathy. Myocardial tissue was obtained from patients with different stages: 1) 25 end-stage tissue obtained at time of left ventricular assist device (LVAD) placement or cardiac transplantation, and 2) 16 post reverse-remodeling: following the removals of LVAD support (average duration: 190±151 days). Twenty-eight of the samples were paired; i.e., obtained from one patient at LVAD implantation and at LVAD removal during transplantation. Samples were from two institutions: 1) Johns Hopkins Hospital in Baltimore, Md. (n=20 patients, n=27 samples) and 2) University of Minnesota in Minneapolis, Minn. (n=7 patients, n=14 samples). Samples from the latter institution were collected and prepared independently, (Chen Y, et al., *Physiol. Genomics*. (2003)) and gene expression data files were kindly provided. The subsequent description applies to the 27 samples collected from patients at the Johns Hopkins Hospital.

All patients had ischemic (n=11) or nonischemic (n=16) end-stage cardiomyopathy with severely reduced ejection fraction, left ventricular dilation, elevated pulmonary arterial and wedge pressures, and reduced cardiac index (Table 1). Importantly, these hemodynamic and remodeling measures were similar between groups. Ischemic cardiomyopathy patients were older, all male, more likely to be on angiotensin-converting enzyme inhibitors (ACEI), and less likely to be on intravenous inotropic therapy.

TABLE 1

Clinical characteristics of patients*

| Clinical Characteristic | Ischemic (11 subjects) | Nonischemic (16 subjects) |
|---|---|---|
| Age, y | 57.5 (54-60) | 46 (37-52)† |
| Male | 100% | 67%‡ |
| Left ventricular ejection fraction, % | 18.8 (15.0-25.0) | 15.0 (10.0-20.0) |
| Left ventricular end-diastolic diameter, cm | 6.8 (6.4-7.3) | 7.4 (6.8-8.3) |
| Pulmonary artery pressure, mm Hg | | |
| Systolic | 49 (35-64) | 50 (45-57) |
| Diastolic | 25 (18-33) | 30 (24-30) |
| Pulmonary capillary wedge pressure, mm Hg | 27 (14-31) | 25 (20-30) |
| Cardiac index, $L \cdot min^1 \cdot m^2$ | 2.2 (1.5-2.4) | 1.5 (1.3-1.9) |
| Medications | | |
| Beta antagonists | 70% | 39% |
| ACE inhibitors or Angiotensin receptor blockers | 100% | 62%† |
| Diuretics | 100% | 69% |
| Intravenous inotropic therapy§ | 10% | 62%† |

*Values are median ($25_{th}$ and $75_{th}$ percentiles) or percentages. Data on left ventricular enddiastolic diameter was available for 8 ischemic patients and 14 nonischemic patients. Data on pulmonary artery systolic and diastolic pressure and pulmonary capillary wedge pressure was available for 8 ischemic patients and 13 nonischemic patients. Data on cardiac index was available for 8 ischemic patients and 11 nonischemic patients. Data on medications was available for 10 nonischemic patients and 13 nonischemic patients.
†$p < 0.05$
‡$p = 0.06$
§Includes dopamine, dobutamine, and milrinone.

Example 2

Sample Allocation and Random Partitioning

Twenty-five of the 41 samples were used for the identification and validation of the gene expression prediction profile. All 25 samples were obtained from patients at the time of LVAD implantation or cardiac transplantation. We used 16 samples as a training set. The gene profile was then tested in 9 samples from different patients, including 7 obtained from microarray analysis at the University of Minnesota. The profile was also tested in 16 post LVAD samples.

To gain insight into the overall predictive power of gene expression profiling, we tested and validated the gene expression prediction profile based on the principle of random partitioning. We considered all 210 possible subdivisions obtained by random sampling, each of which includes 10 ischemic samples divided into 6 training samples and 4 test samples and 15 nonischemic samples divided into 10 training samples and 5 test samples, by random partitioning. (FIG. 1).

Example 3

Diagnostic Accuracy

PAM is designed to use as many as all gene expression measurements on an array. However, because we wanted to determine gene profiling containing a small subset of genes we focused on the 3332 genes selected by SAM. The predictive accuracy of gene expression profiles containing five to all 3332 differentially expressed genes was assessed over all 210 random partitions. Using PAM on our hypothesis-generating set (n=16), we identified a gene expression profile that accurately distinguished ischemic from nonischemic samples. When applied to independent samples generated in a different laboratory, this signature had 100% sensitivity and 100% specificity for the identification of ischemic versus non-ischemic cardiomyopathy. To establish confidence intervals for predictive accuracy of the technique, we used random 210 combinations of training and test sets, revealing a sensitivity of 89% (95% Cl 75-100%) and a specificity of 89% (95% Cl 60-100%).

The genes in the prediction profile were visualized by hierarchical clustering and a heat map (Eisen M B, et al., Proc Natl Acad Sci. (1998)) using Euclidean distance with complete linkage.

To assess whether the significant differences in clinical parameters between ischemic and nonischemic samples contributed to the profile's accuracy, we examined the predictive accuracy in strata based on each clinical covariate (Table 2). Within the strata, the sensitivity and specificity were similar and were all comparable to the overall sensitivity and specificity (Table 2).

TABLE 2

Sensitivity and Specificity of 90-gene profile in strata defined by clinical covariates

|  | Sensitivity | Specificity |
|---|---|---|
| Overall | 89% | 89% |
| Age, y |  |  |
| ≧50 | 88% | 80% |
| <50 | 100% | 90% |
| Gender |  |  |
| Female | n/a | 100% |
| Male | 90% | 80% |
| Ejection fraction, % |  |  |
| ≧15 | 89% | 89% |
| <15 | 100% | 83% |
| ACEI |  |  |
| Yes | 90% | 80% |
| No | n/a | 100% |
| Inotropic therapy |  |  |
| Yes | 100% | 100% |
| No | 89% | 60% |

ACEI denotes angiotensin-converting enzyme inhibitor

Example 4

Post-LVAD Analysis

To assess whether the expression-based prediction profile was affected by the stage of heart failure, we assessed its accuracy in 16 post-LVAD samples. The gene expression profile correctly classified all nonischemic samples (specificity 100%), but only classified one ischemic sample correctly (sensitivity 33%).

Example 5

Characterization of the Gene Expression Molecular Signature

Figure 2:
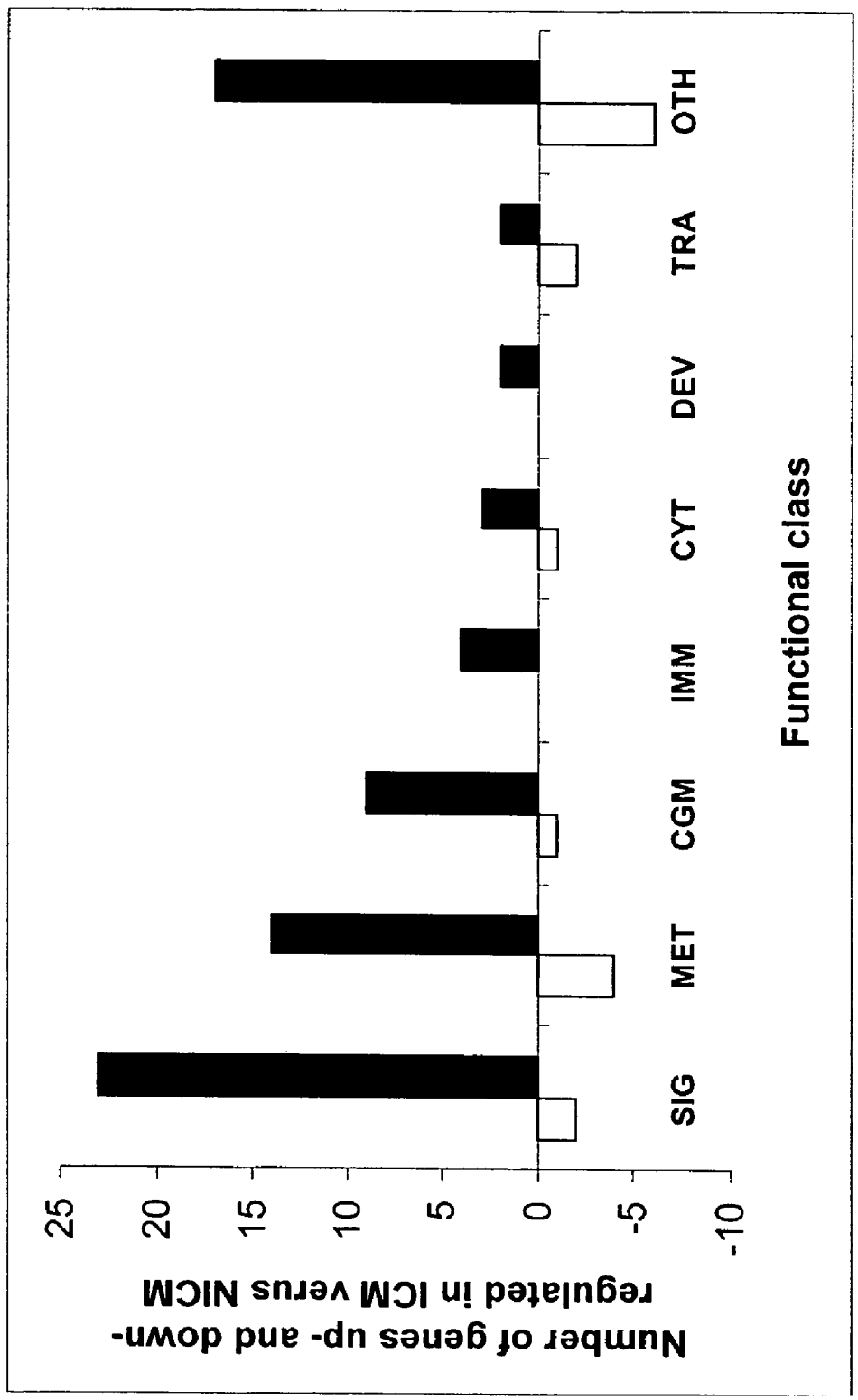
FIG. 2 is a bargraph showing the number of genes up- and down-regulated in ischemic hearts relative to nonischemic hearts classified by functional group (www.geneontology.org).

Over all 210 combinations of training and test set samples, the greatest accuracy was achieved with profiles containing 90 genes, and 30% of the time, the 90-gene expression profile exhibited perfect accuracy (Table 3). The average accuracy of 210 combinations are shown in Table 3. The majority of genes fell into functional groups of signal transduction, metabolism, and cell growth/maintenance (FIG. 2). The majority of genes had up-regulated expression in ischemic hearts as compared to nonischemic hearts with an average fold change of 1.9.+−.0.9.

TABLE 3

Gene expression prediction profile

| Gene accession no. | Gene symbol | Gene name | Fold change* |
|---|---|---|---|
| *Cell growth/maintenance* | | | |
| AL078621 | RPL23AP7 | ribosomal protein L23a pseudogene 7 | 2.4 |
| AA086229 | ENIGMA | enigma (LIM domain protein) | 2.2 |

TABLE 3-continued

Gene expression prediction profile

| Gene accession no. | Gene symbol | Gene name | Fold change* |
|---|---|---|---|
| NM_005938 | MLLT7 | myeloid/lymphoid or mixed-lineage leukemia | 2 |
| AA054734 | CIZ1 | CDKN1A interacting zinc finger protein 1 | 1.6 |
| AA576621 | CDC2L5 | cell division cycle 2-like 5 | 1.5 |
| NM_000076 | CDKN1C | cyclin-dependent kinase inhibitor 1C (p57, Kip2) | 1.5 |
| NM_003547 | HIST1H4G | histone 1, H4g | 1.5 |
| BC005174 | ATF5 | activating transcription factor 5 | 1.4 |
| NM_015487 | GEMIN4 | gem (nuclear organelle) associated protein 4 | 1.4 |
| BC000229 | MIS12 | homolog of yeast Mis12 | −1.5 |
| Cytoskeleton | | | |
| U40572 | SNTB2 | syntrophin, beta 2 | 1.9 |
| NM_007284 | PTK9L | protein tyrosine kinase 9-like | 1.8 |
| AI077476 | DMN | desmuslin | 1.5 |
| NM_014016 | SACM1L | SAC1 suppressor of actin mutations 1-like (yeast) | −1.9 |
| Development | | | |
| NM_001420 | ELAVL3 | Hu antigen C | 2.5 |
| AF005081 | NA | *Homo sapiens* skin-specific protein (xp32) mRNA | 2 |
| Immune response | | | |
| NM_030882 | APOL2 | apolipoprotein L, 2 | 2.4 |
| NM_030754 | SAA2 | serum amyloid A2 | 2.4 |
| L34163 | IGHM | immunoglobulin heavy constant mu | 2.3 |
| AA742237 | BAT2 | HLA-B associated transcript 2 | 2 |
| Metabolism | | | |
| AW134794 | SLC39A8 | solute carrier family 39 (zinc transporter), member 8 | 2.7 |
| AI379894 | PPP2CB | protein phosphatase 2 (formerly 2A), catalytic subunit, beta isoform | 2.2 |
| BC004864 | PPP3CC | protein phosphatase 3 (formerly 2B), catalytic subunit, gamma isoform (calcineurin A gamma) | 2.2 |
| NM_002779 | PSD | pleckstrin and Sec7 domain protein | 2.2 |
| NM_006782 | ZFPL1 | zinc finger protein-like 1 | 2.2 |
| U94357 | GYG2 | glycogenin 2 | 2.1 |
| NM_003456 | ZNF205 | zinc finger protein 205 | 2.1 |
| BC005043 | MGC31957 | hypothetical protein MGC31957 | 1.9 |
| NM_014649 | SAFB2 | scaffold attachment factor B2 | 1.8 |
| NM_018135 | MRPS18A | mitochondrial ribosomal protein S18A | 1.7 |
| NM_007188 | ABCB8 | ATP-binding cassette, sub-family B (MDR/TAP), member 8 | 1.6 |
| NM_018411 | HR | hairless homolog (mouse) | 1.6 |
| NM_006238 | PPARD | peroxisome proliferative activated receptor, delta | 1.6 |
| AA047234 | OAZIN | ornithine decarboxylase antizyme inhibitor | 1.4 |
| NM_005254 | GABPB1 | GA binding protein transcription factor, beta subunit 1 (53 kD) | −1.5 |
| NM_015906 | TRIM33 | tripartite motif-containing 33 | −1.6 |
| AL525798 | FACL3 | fatty-acid-Coenzyme A ligase, long-chain 3 | −1.7 |
| NM_004457 | FACL3 | fatty-acid-Coenzyme A ligase, long-chain 3 | −2 |
| Signal transduction | | | |
| D10202 | PTAFR | platelet-activating factor receptor | 2.6 |
| NM_014716 | CENTB1 | centaurin, beta 1 | 2.5 |
| BC005365 | MAP2K7 | *Homo sapiens*, clone IMAGE: 3829438, mRNA, partial cds | 2.3 |
| AI860917 | PNUTL1 | peanut-like 1 (*Drosophila*) | 2.3 |
| AI688812 | RASGRP2 | RAS guanyl releasing protein 2 (calcium and DAG-regulated) | 2.3 |
| AF028825 | DLG4 | discs, large (*Drosophila*) homolog 4 | 2.2 |
| NM_007327 | GRIN1 | glutamate receptor, ionotropic, N-methyl Daspartate 1 | 2.2 |
| NM_006869 | CENTA1 | centaurin, alpha 1 | 2.1 |
| AJ133822 | AGER | advanced glycosylation end product-specific receptor | 2 |
| NM_007369 | RE2 | G-protein coupled receptor | 2 |
| AW138374 | RHEB | Ras homolog enriched in brain 2 | 2 |
| X60502 | SPN | sialophorin (gpL115, leukosialin, CD43) | 2 |
| M24900 | THRA | thyroid hormone receptor, alpha | 2 |
| NM_001397 | ECE1 | endothelin converting enzyme 1 | 1.9 |
| L05666 | GRIN1 | glutamate receptor, ionotropic, N-methyl Daspartate 1 | 1.8 |
| AF287892 | SIGLEC8 | sialic acid binding Ig-like lectin 8 | 1.8 |
| NM_014274 | TRPV6 | transient receptor potential cation channel, subfamily V, member 6 | 1.8 |
| NM_000479 | AMH | anti-Mullerian hormone | 1.7 |

TABLE 3-continued

Gene expression prediction profile

| Gene accession no. | Gene symbol | Gene name | Fold change* |
|---|---|---|---|
| NM_014204 | BOK | BCL2-related ovarian killer | 1.7 |
| U58856 | MRC2 | mannose receptor, C type 2 | 1.6 |
| AI991328 | CHK | choline kinase | 1.5 |
| NM_000908 | NPR3 | atrionatriuretic peptide receptor C | 1.4 |
| BG222394 | MAPK8IP1 | mitogen-activated protein kinase 8 interacting protein 1 | 1.3 |
| AA460694 | KIAA1354 | KIAA1354 protein | −1.6 |
| BG111761 | GNG12 | guanine nucleotide binding protein (G protein), gamma 12 | −1.8 |
| | | Transport | |
| U87555 | SCN2B | sodium channel, voltage-gated, type II, beta polypeptide | 2.1 |
| NM_024681 | FLJ12242 | hypothetical protein FLJ12242 | 2 |
| W72053 | TGOLN2 | trans-golgi network protein 2 | −1.6 |
| AJ131244 | SEC24A | SEC24 related gene family, member A (*S. cerevisiae*) | −2 |
| | | Other | |
| AK025352 | MAST205 | microtubule associated testis specific serine/threonine protein kinase | 2.3 |
| AI818951 | MGC40499 | hypothetical protein MGC4049 | 2.3 |
| AK025188 | FLJ20699 | hypothetical protein FLJ20699 | 2.2 |
| AI831055 | SFTPC | surfactant, pulmonary-associated protein C | 2.2 |
| BC004264 | EPHB4 | ephrin receptor | 2.1 |
| NM_031304 | MGC4293 | hypothetical protein MGC4293 | 2.1 |
| D38024 | DUX4 | double homeobox, 4 | 1.9 |
| NM_003061 | SLIT1 | slit homolog 1 (*Drosophila*) | 1.9 |
| NM_024821 | FLJ22349 | hypothetical protein FLJ22349 | 1.8 |
| NM_019858 | GRCA | likely ortholog of mouse gene rich cluster, A gene | 1.8 |
| AF023203 | NA | *Homo sapiens* homeobox protein Og12 (OGL12) mRNA | 1.8 |
| NM_030935 | THG-1 | TSC-22-like | 1.8 |
| NM_025268 | MGC4659 | hypothetical protein MGC4659 | 1.6 |
| BC000979 | DDX49 | DEAD (Asp-Glu-Ala-Asp) box polypeptide 49 | 1.5 |
| AK021505 | NA | *Homo sapiens* cDNA FLJ11443 fis, clone HEMBA1001330 | 1.5 |
| NM_018049 | GNRPX | likely ortholog of mouse guanine nucleotide releasing protein x | 1.4 |
| AA018777 | NA | ESTs, Weakly similar to ALU7_HUMAN ALU SUBFAMILY SQ SEQUENCE | 1.2 |
| AF052151 | MTVR1 | Mouse Mammary Tumor Virus Receptor homolog 1 | −1.3 |
| AL525412 | MYCBP | Mycbp-associated protein | −1.4 |
| NM_012311 | KIN | antigenic determinant of recA protein homolog (mouse) | −1.5 |
| NM_018553 | HSA277841 | ELG protein | −1.6 |
| AA191576 | NPM1 | nucleophosmin | −1.6 |
| NM_016628 | WAC | WW domain-containing adapter with a coiled-coil region | −1.8 |

*Fold change described the mean gene expression for ischemic samples relative to nonischemic samples.

Figure 3:
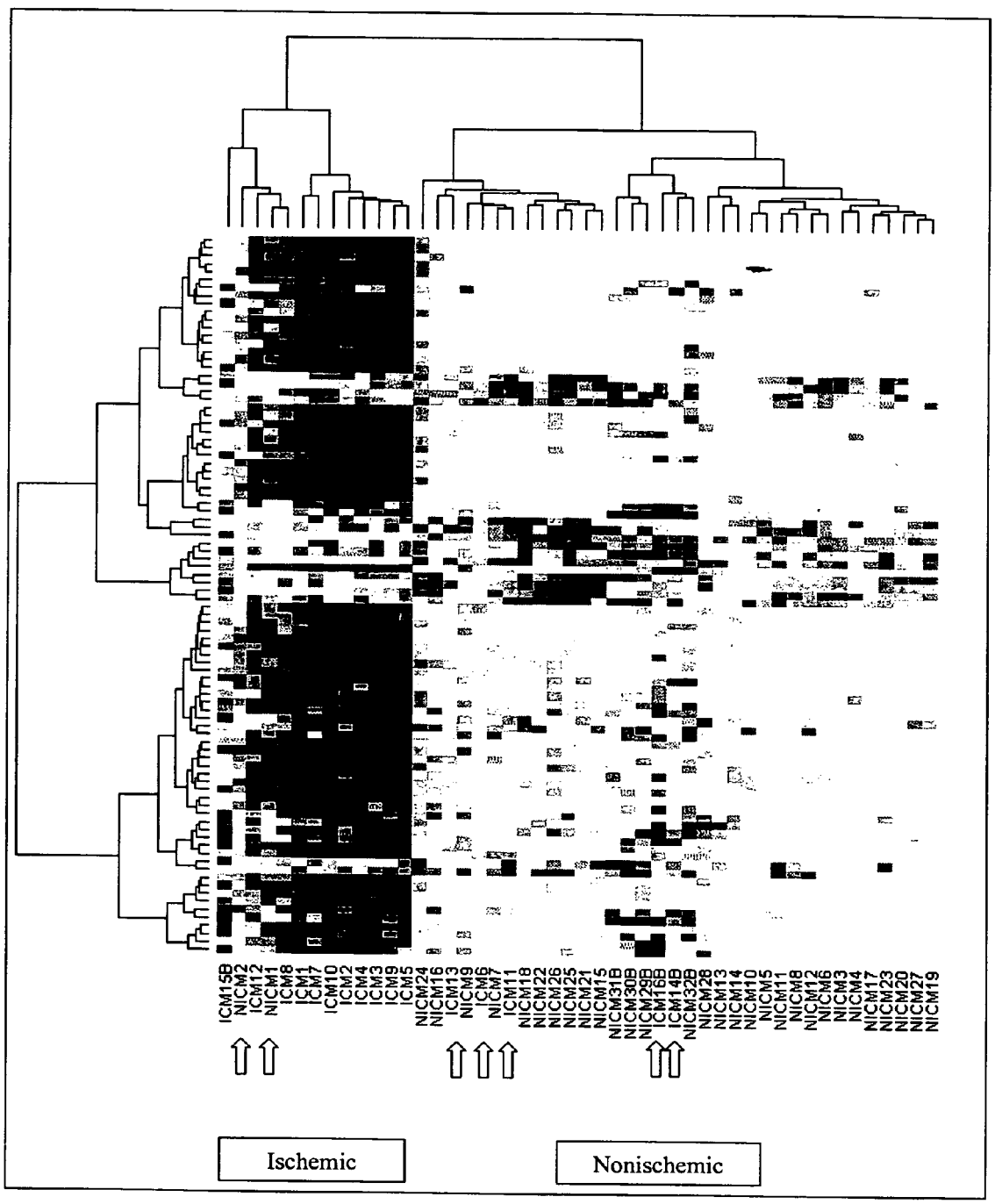
FIG. 3 is a hierarchical clustering of 90 genes in 48 samples based on similarity in gene expression and relatedness of samples. Each row represents a gene labeled with the gene symbol and each column represents a sample. The color in each cell reflects the level of expression of the corresponding gene in the corresponding sample, relative to its mean level of expression in the entire set of samples. Expression levels greater than the mean are shaded in blue, and those below the mean are shaded in red. The samples form two distinct clusters based on etiology. Arrows denote samples that do not appear in their etiology cluster. ICM denotes ischemic cardiomyopathy and NICM denotes nonischemic cardiomyopathy.

In a hierarchical clustering algorithm of the 90-gene expression prediction profile, all but three of the ischemic samples form a distinct cluster, and all but one of the nonischemic samples form a distinct cluster (FIG. 3). Importantly, the samples did not cluster by pre- or post-LVAD status or by institution of origin.

The invention is not limited by the embodiments described above which are presented as examples only but can be modified in various ways within the scope of protection defined by the appended patent claims.

Thus, while we have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

A list of pertinent publications follows, the contents of which are incorporated by reference in their entirety.
1. Alizadeh A A, Eisen M B, Davis R E et al. Distinct types of diffuse large B-cell lymphoma identified by gene expression profiling. *Nature*. 2000; 403:503-511.
2. Lapointe J, Li C, Higgins J P et al. Gene expression profiling identifies clinically relevant subtypes of prostate cancer. *Proc Natl Acad Sci USA*. 2004; 101:811-816.

3. Tibshirani R, Hastie T, Narasimhan B et al. Diagnosis of multiple cancer types by shrunken centroids of gene expression. *Proc Natl Acad Sci USA.* 2002; 99:6567-6572.
4. Dhanasekaran S M, Barrette T R, Ghosh D et al. Delineation of prognostic biomarkers in prostate cancer. *Nature.* 2001; 412:822-826.
5. Pomeroy S L, Tamayo P, Gaasenbeek M et al. Prediction of central nervous system embryonal tumour outcome based on gene expression. *Nature.* 2002; 415:436-442.
6. van de Vijver M J, He Y D, van't Veer L J et al. A gene-expression signature as a predictor of survival in breast cancer. *N Engl J Med.* 2002; 347:1999-2009.
7. Golub T R, Slonim D K, Tamayo P et al. Molecular classification of cancer: class discovery and class prediction by gene expression monitoring. *Science.* 1999; 286:531-537.
8. Rosenwald A, Wright G, Chan W C et al. The use of molecular profiling to predict survival after chemotherapy for diffuse large-B-cell lymphoma. *N Engl J Med.* 2002; 346:1937-1947.
9. Agendia working to develop first microarray-based breast cancer test using Agilent Technologies' gene expression platform. http://www.agilent.com/about/newsroom/pres-rel/2003/21aug2003a.html. 2004. Mar. 16, 2004. Ref Type: Electronic Citation
10. Barrans J D, Allen P D, Stamatiou D et al. Global gene expression profiling of end-stage dilated cardiomyopathy using a human cardiovascular-based cDNA microarray. *Am J Pathol.* 2002; 160:2035-2043.
11. Tan F L, Moravec C S, Li J et al. The gene expression fingerprint of human heart failure. *Proc Natl Acad Sci USA.* 2002; 99:11387-11392.
12. Yung C K, Halperin V L, Tomaselli G F et al. Gene expression profiles in end-stage human idiopathic dilated cardiomyopathy: altered expression of apoptotic and cytoskeletal genes. *Genomics.* 2004; 83:281-297.
13. Steenman M, Chen Y W, Le Cunff M et al. Transcriptional analysis of failing and nonfailing human hearts. *Physiol Genomics.* 2003; 12:97-112.
14. Hwang J J, Allen P D, Tseng G C et al. Microarray gene expression profiles in dilated and hypertrophic cardiomyopathic end-stage heart failure. *Physiol Genomics.* 2002; 10:31-44.
15. Chen Y, Park S, Li Y et al. Alterations of gene expression in failing myocardium following left ventricular assist device support. *Physiol Genomics.* 2003; 14:251-260.
16. Hall J L, Grindle S, Han X et al. Genomic Profiling of the Human Heart Before and After Mechanical Support with a Ventricular Assist Device Reveals Alterations in Vascular Signaling Networks. *Physiol Genomics.* 2004.
17. Chen M M, Ashley E A, Deng D X et al. Novel role for the potent endogenous inotrope apelin in human cardiac dysfunction. *Circulation.* 2003; 108:1432-1439.
18. Blaxall B C, Tschannen-Moran B M, Milano Calif. et al. Differential gene expression and genomic patient stratification following left ventricular assist device support. *J Am Coll Cardiol.* 2003; 41:1096-1106.
19. Felker G M, Thompson R E, Hare J M et al. Underlying causes and long-term survival in patients with initially unexplained cardiomyopathy. *N Engl J Med.* 2000; 342: 1077-1084.
20. Felker G M, Benza R L, Chandler A B et al. Heart failure etiology and response to milrinone in decompensated heart failure: results from the OPTIME-CHF study. *J Am Coll Cardiol.* 2003; 41:997-1003.
21. Dries D L, Sweitzer N K, Drazner M H et al. Prognostic impact of diabetes mellitus in patients with heart failure according to the etiology of left ventricular systolic dysfunction. *J Am Coll Cardiol.* 2001; 38:421-428.
22. Kittleson M, Hurwitz S, Shah M R et al. Development of circulatory-renal limitations to angiotensin-converting enzyme inhibitors identifies patients with severe heart failure and early mortality. *J Am Coll Cardiol.* 2003; 41:2029-2035.
23. Doval H C, Nul D R, Grancelli H O et al. Randomised trial of low-dose amiodarone in severe congestive heart failure. Grupo de Estudio de la Sobrevida en la Insuficiencia Cardiaca en Argentina (GESICA). *Lancet.* 1994; 344:493-498.
24. Singh S N, Fletcher R D, Fisher S G et al. Amiodarone in patients with congestive heart failure and asymptomatic ventricular arrhythmia. Survival Trial of Antiarrhythmic Therapy in Congestive Heart Failure. *N Engl J Med.* 1995; 333:77-82.
25. Follath F, Cleland J G, Klein W et al. Etiology and response to drug treatment in heart failure. *J Am Coll Cardiol.* 1998; 32:1167-1172.
26. Hare J M, Walford G D, Hruban R H et al. Ischemic cardiomyopathy: endomyocardial biopsy and ventriculographic evaluation of patients with congestive heart failure, dilated cardiomyopathy and coronary artery disease. *J Am Coll Cardiol.* 1992; 20:1318-1325.
27. Felker G M, Shaw L K, O'Connor C M. A standardized definition of ischemic cardiomyopathy for use in clinical research. *J Am Coll Cardiol.* 2002; 39:210-218.
28. Bioconductor Homepage. www.bioconductor.org. 2004. Dec. 1, 2003. Ref Type: Electronic Citation
29. Eisen M B, Spellman P T, Brown P O et al. Cluster analysis and display of genome-wide expression patterns. *Proc Natl Acad Sci USA.* 1998; 95:14863-14868.
30. Gene Ontology Consortium Homepage. www.geneontology.org. 2004. Dec. 1, 2003. Ref Type: Electronic Citation
31. Hastie T, Tibshirani R, Eisen M B et al. 'Gene shaving' as a method for identifying distinct sets of genes with similar expression patterns. *Genome Biol.* 2000; 1:RESEARCH0003.
32. Sarwal M, Chua M S, Kambham N et al. Molecular heterogeneity in acute renal allograft rejection identified by DNA microarray profiling. *N Engl J Med.* 2003; 349:125-138.
33. Reynolds M R, Josephson M E. MADIT II (second Multicenter Automated Defibrillator Implantation Trial) debate: risk stratification, costs, and public policy. *Circulation.* 2003; 108:1779-1783.
34. Mukherjee S, Tamayo P, Rogers S et al. Estimating dataset size requirements for classifying DNA microarray data. *J Comput Biol.* 2003; 10:119-142.
35. Boheler K R, Volkova M, Morrell C et al. Sex- and age-dependent human transcriptome variability: implications for chronic heart failure. *Proc Natl Acad Sci USA.* 2003; 100:2754-2759.
36. Cook S A, Rosenzweig A. DNA microarrays: implications for cardiovascular medicine. *Circ Res.* 2002; 91:559-564.
37. Irizarry R A, Hobbs B, Collin F et al. Exploration, normalization, and summaries of high density oligonucleotide array probe level data. *Biostatistics.* 2003; 4:249-264.
38. Irizarry R A, Bolstad B M, Collin F et al. Summaries of Affymetrix GeneChip probe level data. *Nucleic Acids Res.* 2003; 31:e15.
39. Tusher V G, Tibshirani R, Chu G. Significance analysis of microarrays applied to the ionizing radiation response. *Proc Natl Acad Sci USA.* 2001; 98:5116-5121.

We claim:

1. A method for distinguishing ischemic from nonischemic cardiomyopathy, comprising the steps of:
   (a) obtaining a clinical specimen from a patient suffering from cardiomyopathy;
   (b) detecting the expression level(s) of a set of genes in the clinical specimen, wherein the set of genes comprises the following genes: RPL23AP7, ENIGMA, MLLT7, CIZ1, CDC2L5, CDKN1C, HIST1H4G, ATF5, GEMIN4, MIS12, SNTB2, PTK9L, DMN, SACM1L, ELAVL3, APOL2, SAA2, IGHM, BAT2, SLC39A8, PPP2CB, PPP3CC, PSD, ZFPL1, GYG2, ZNF205, MGC31957, SAFB2, MRPS18A, ABCB8, HR, PPARD, OAZIN, GABPB1, TRIM33, PTAFR, CENTB 1, MAP2K7, PNUTL1, RASGRP2, DLG4, CENTA1, AGER, RE2, RHEB, SPN, THRA, ECE1, SIGLEC8, TRPV6, AMH, BOK, MRC2, CHK, NPR3, MAPK8IP1, KIAA1354, GNG12, SCN2B, FLJ12242, TGOLN2, SEC24A, MAST205, MGC40499, FLJ20699, SFTPC, EPHB4, MGC4293, DUX4, SLIT1, FLJ22349, GRCA, THG-1, MGC4659, DDX49, GNRPX, MTVR1, MYCBP, KIN, HSA277841, NPM1 and WAG;
   (c) comparing the expression level(s) of the set of genes in the clinical specimen with expression level(s) of a gene expression prediction profile associated with ischemic or nonischemic cardiomyopathy.

2. The method of claim 1, wherein the clinical specimen is obtained from myocardial tissue prior to installation of a left ventricular assist device (LVAD).

3. The method of claim 1, wherein the clinical specimen is obtained from myocardial tissue after removal of a left ventricular assist device (LVAD).

4. The method of claim 1, wherein the clinical specimen is obtained from endomyocardial biopsy.

5. The method of claim 1, wherein Significance Analysis of Microarrays (SAM) is used in comparing the expression level(s) of the one or more gene(s) in the clinical specimen with expression level(s) of a gene expression profile associated with ischemic or nonischemic cardiomyopathy.

6. The method of claim 1, wherein Prediction Analysis of Microarray (PAM) is used in comparing the expression level(s) of the one or more gene(s) in the clinical specimen with expression level(s) of a gene expression profile associated with ischemic or nonischemic cardiomyopathy.

7. The method of claim 1, wherein the one or more gene(s) have up-regulated expression in ischemic hearts as compared to nonischemic hearts.

8. The method of claim 1, wherein the one or more gene(s) have down-regulated expression in ischemic hearts as compared to nonischemic hearts.

9. A method for distinguishing ischemic from nonischemic cardiomyopathy, comprising the steps of:
   (a) obtaining a clinical specimen from a patient suffering from cardiomyopathy;
   (b) detecting the expression level(s) of a set of genes in the clinical specimen; wherein said set of genes is selected from PPP2CB, SAA2 and MAP2K7, and
   (c) comparing the expression level(s) of the set of genes in the clinical specimen with expression level(s) of a gene expression prediction profile associated with ischemic or nonischemic cardiomyopathy.

10. The method of claim 9, wherein said PPP2CB gene exhibits up-regulation in ischemic hearts relative to non-ischemic hearts and is characterized by a mean gene expression fold change of 2.2.

11. The method of claim 9, wherein said SAA2 gene exhibits up-regulation in ischemic hearts relative to non-ischemic hearts and is characterized by a mean gene expression fold change of 2.4.

12. The method of claim 9, wherein said MAP2K7 gene exhibits up-regulation in ischemic hearts relative to non-ischemic hearts and is characterized by a mean gene expression fold change of 2.3.

* * * * *

UNITED STATES PATENT AND TRADEMARK OFFICE
CERTIFICATE OF CORRECTION

PATENT NO. : 7,592,138 B2 Page 1 of 1
APPLICATION NO. : 11/012778
DATED : September 22, 2009
INVENTOR(S) : Hare et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 808 days.

Signed and Sealed this

Twenty-first Day of September, 2010

David J. Kappos
*Director of the United States Patent and Trademark Office*